United States Patent [19]

Paparizos et al.

[11] Patent Number: 5,183,793
[45] Date of Patent: Feb. 2, 1993

[54] AMMOXIDATION CATALYSTS AND METHODS FOR THEIR PREPARATION FOR USE IN THE PRODUCTION OF ISOPHTHALONITRILE

[75] Inventors: Christos Paparizos, Willownick; Wilfrid G. Shaw, Lyndhurst, both of Ohio

[73] Assignee: The Standard Oil Company, Cleveland, Ohio

[21] Appl. No.: 789,836

[22] Filed: Nov. 13, 1991

[51] Int. Cl.$^5$ .............................................. B01J 23/84
[52] U.S. Cl. ...................................... 502/338; 502/178; 502/205; 502/209; 502/215; 502/304; 502/312; 502/324; 502/328; 502/330; 502/331; 558/327; 558/328
[58] Field of Search ............... 558/327, 328; 502/338, 502/205, 209, 215, 304, 312, 328, 330, 331

[56] References Cited

U.S. PATENT DOCUMENTS

| | | | |
|---|---|---|---|
| 2,839,535 | 6/1958 | Hadley et al. | 260/294.9 |
| 3,029,245 | 4/1962 | Aries | 260/294.9 |
| 3,231,600 | 1/1966 | Jones et al. | 260/465 |
| 3,312,710 | 4/1967 | Sakayama et al. | 260/294.9 |
| 3,435,061 | 3/1969 | Grasselli et al. | 260/465 |
| 3,489,787 | 1/1970 | Stiles | 260/465.3 |
| 3,542,843 | 11/1970 | Yoshino et al. | 260/465.3 |
| 3,544,617 | 12/1970 | Oga et al. | 260/465 |
| 3,555,021 | 1/1971 | Beutel et al. | 260/250 |
| 3,591,620 | 7/1971 | Yoshino et al. | 260/465.3 |
| 3,637,797 | 1/1972 | Decker et al. | 260/465 C |
| 3,716,496 | 2/1973 | Yoshino et al. | 252/439 |
| 3,801,619 | 4/1974 | Botte et al. | 260/465 C |
| 3,803,204 | 4/1974 | Grasselli et al. | 260/465 C |
| 3,812,171 | 5/1974 | Neikam | 260/465 C |
| 3,839,398 | 10/1974 | Leto et al. | 260/465 C |
| 3,845,094 | 10/1974 | Angstadt | 260/465 C |
| 3,868,400 | 2/1975 | Norton | 260/464 |
| 3,870,743 | 3/1975 | Ibing et al. | 260/465 C |
| 3,901,900 | 8/1975 | Angstadt et al. | 260/294.9 |
| 3,923,819 | 12/1975 | Lüssling et al. | 260/294.9 |
| 3,926,856 | 12/1975 | Lüssling et al. | 252/470 |
| 3,927,007 | 12/1975 | Lüssling et al. | 260/294.9 |
| 3,959,336 | 5/1976 | Bushick et al. | 260/465 C |
| 3,959,337 | 5/1976 | Bushick et al. | 260/465 C |
| 3,988,359 | 10/1976 | Saito et al. | 260/465.3 |
| 4,018,713 | 4/1977 | Bushick et al. | 252/464 |
| 4,044,042 | 8/1977 | Angstadt | 260/465 C |
| 4,062,885 | 12/1977 | Mekhtiev et al. | 260/465 C |
| 4,065,487 | 12/1977 | Rizaev et al. | 260/465 C |
| 4,092,271 | 5/1978 | Sze | 252/455 R |
| 4,148,757 | 4/1979 | Brazdil et al. | 252/432 |
| 4,170,570 | 10/1979 | Zagata et al. | 252/437 |
| 4,178,304 | 12/1979 | Litvishkov et al. | 260/465 E |
| 4,189,580 | 2/1980 | Findeisen | 544/301 |
| 4,212,766 | 7/1980 | Brazdil et al. | 252/432 |
| 4,214,087 | 7/1980 | Fanelli et al. | 546/319 |
| 4,284,781 | 8/1981 | Sze | 546/286 |
| 4,309,361 | 1/1982 | Suresh et al. | 260/465.3 |
| 4,336,205 | 6/1982 | Onishi et al. | 260/465 C |
| 4,410,450 | 10/1983 | Sasaki et al. | 502/22 |
| 4,415,482 | 11/1983 | Ebner | 502/205 |
| 4,439,371 | 3/1984 | Rizaev et al. | 260/465 C |
| 4,504,599 | 3/1985 | Sasaki et al. | 502/304 |

FOREIGN PATENT DOCUMENTS 1227623 4/1986 U.S.S.R. ............................ 558/327

Primary Examiner—W. J. Shine
Attorney, Agent, or Firm—Dilworth & Barrese

[57] ABSTRACT

Catalysts having the general formula:

$$V_1Bi_aSb_bFe_cX_dY_c^oZ_fO_g$$

wherein,
X = Mo, Cu, W, Nb, Te, P, Sn, Ge, As
Y = Co, Ni, Ce, La, Mn, Cr
Z = Alkali, alkaline earth, B, Tl and,
a = 0.1–10, b = 0.01–20, c = 0.01–5, d = 0–5, e = o–3, f = 0–1, and g is determined by the valance requirements of the elements present, are produced by first forming and calcining an iron-antimony oxide composition which is subsequently combined with compounds of vanadium, bismuth and other elements. The catalysts are useful in the formation of phthalonitriles from the reaction of xylenes with oxygen and ammonia at elevated temperatures.

9 Claims, No Drawings

AMMOXIDATION CATALYSTS AND METHODS FOR THEIR PREPARATION FOR USE IN THE PRODUCTION OF ISOPHTHALONITRILE

FIELD OF THE INVENTION

This invention relates generally to catalysts for ammoxidation reactions and methods for preparing such catalysts. More particularly, this invention relates to a method for the production of phthalonitrile by reaction of xylenes with oxygen and ammonia at elevated temperature in the presence of catalysts containing vanadium and bismuth oxides and a metal-antimony composition.

BACKGROUND OF THE INVENTION

Phthalonitriles are very versatile chemical intermediates and therefore are technically valuable compounds. Phthalonitriles are used to produce compounds which are important in the production of polymers for synthetic fibers, films and moldings, polyesters, polyimides and epoxy resins, rubber chemicals, agricultural chemicals and pharmaceuticals.

The reaction between alkylbenzene, ammonia and oxygen in the presence of a catalyst and methods for the preparation of appropriate catalysts are generally known (See, for example, U.S. Pat. Nos. 4,336,205, 4,284,781, 4,189,580). Also known are methods for preparing phthalonitriles by oxidative ammonolysis (ammoxidation) of xylene in the presence of a catalyst consisting of a mixture of metal oxides deposited onto a catalyst support. Specifically, the synthesis of phthalonitriles from xylenes by oxidative ammonolysis, including synthesis of isophthalonitrile from m-xylene using a catalyst composed of antimony oxide, bismuth oxide, vanadium oxide or molybdenum oxide, and ferric oxide on a carrier which is preferably silica gel or alumina has been described in U.S. Pat. No. 4,439,371.

The ammoxidation of m-xylene to isophthalonitrile utilizing a catalyst comprising a mixture of vanadium oxide and molybdenum oxide on an alumina carrier which is activated with at least one of cerium, chromium, manganese, tungsten, bismuth, tin, antimony, titanium, lithium, sodium, and potassium is described in U.S. Pat. No. 3,870,743.

U.S. Pat. No. 3,870,743 describes a method for preparing phthalonitriles by way of oxidative ammonolysis of xylenes at temperatures in the range of 300° C. to 600° C. and the contact time of 0.1 to 4 seconds.

A principal disadvantage of the above-discussed methods resides in an insufficient per pass conversion of the desired product and a low isophthalonitrile selectivity of the catalyst. Thus, improvements to the product per pass conversion and the isophthalonitrile selectivity of the catalyst would be welcome improvements to the art.

It is, accordingly, an object of the present invention to provide a catalyst for the preparation of isophthalonitrile from m-xylene by ammoxidation at elevated temperatures having improved product per pass conversion and increased product selectivity of the catalyst.

SUMMARY OF THE INVENTION

This and other objects are realized in accordance with the present invention by ammoxidation catalyst compositions of the general formula:

$$V_1Bi_aSb_bFe_cX_dY_eZ_fO_g$$

wherein,
X = Mo, Cu, W, Nb, Te, P, Sn, Ge, As
Y = Co, Ni, Ce, La, Mn, Cr
Z = Alkali, alkaline earth, B, Tl and,
a = 0.1–10, b = 0.01–20, c = 0.01–5, d = 0–5, e = 0–3, f = 0–1, and g is determined by the valance requirements of the other elements present. The catalysts of this invention are further characterized in that in preparing the catalysts an iron-antimony oxide composition is pre-formed and calcined before admixture with the other catalyst components. In another aspect the invention relates to methods for producing an ammoxidation catalyst, the method comprising the steps of:

a) pre-forming and calcining an iron-antimony oxide composition;

b) preparing the catalyst including the said preformed composition, vanadium and bismuth compounds and any other optional materials; said catalyst optionally containing a support material.

In yet another aspect, this invention embraces methods of producing isophthalonitrile by reacting m-xylene with oxygen and ammonia in the presence of the aforementioned novel catalysts.

DESCRIPTION OF THE PREFERRED EMBODIMENTS

The catalysts of the present invention can be used to catalyze a variety of ammoxidation reactions, including the ammoxidation of dialkylbenzenes such as, for example m-xylene, whether pure or very crude. The catalysts of the present invention are particularly useful in the production of isophthalonitrile by the reaction of m-xylene with oxygen and ammonia at elevated temperatures.

Ammoxidation catalysts in accordance with the present invention have the general formula:

$$V_1Bi_aSb_bFe_cX_dY_eZ_fO_g$$

wherein,
X = Mo, Cu, W, Nb, Te, P, Sn, Ge, As
Y = Co, Ni, Ce, La, Mn, Cr
Z = Alkali, alkaline earth, B, Tl and,
a = 0.1–10, b = 0.01–20, c = 0.01–5, d = 0–5, e = 0–3, f = 0–1, and g is determined by the valence requirements of the other elements present.

While the catalysts of the invention generally may be prepared in any known manner, their preparation includes the step of pre-forming an iron-antimony composition, which pre-formed composition is subsequently combined with other metal compounds to provide the final catalyst. In addition, other metals may be pre-formed with antimony, including molybdenum, cerium and tin.

Such pre-formed metal-antimony compositions may be prepared by any one of a number of different methods, the particular method employed being a matter of convenience. For example, the composition may be prepared by mixing the ingredients in an aqueous mixture, drying the resulting solution and subsequently calcining the product. The ingredients can be added in any order during the preparation procedure. The ingredients employed can be the oxides, nitrates, acetates or other compounds of the metal and antimony, and particularly preferred is the use of water soluble salts of the metals. One method of preparation of the pre-formed iron-antimony composition comprises refluxing a suspension of $Sb_2O_3$ and $Fe(NO_3)_3.9H_2O$ in $H_2O$ and $HNO_3$, evaporating the obtained mixture to dryness and calcining at about 750° C.

The pre-forming of the iron-antimony composition includes the calcining of this composition using known techniques before incorporation into the catalyst of the present invention. The calcining temperature is dictated by the starting materials. Generally, a calcining temperature of about 700° C. to about 1000° C. is suitable. A preferred calcining temperature is from about 720° C. to about 850° C.

Once the iron-antimony composition is pre-formed including calcining catalysts of the present invention may be prepared by any one of a number of different methods, the particular method employed being a matter of convenience. In one embodiment, the catalyst may be prepared by mixing the appropriate catalyst ingredients and optionally, the support material, in an aqueous mixture, drying the resulting slurry and subsequently calcining the product. The ingredients may be added in any order during the preparation procedure but certain orders may be preferred. The ingredients employed can be the oxides, nitrates, acetates or other compounds of the particular metals or elements added, and particularly useful is the use of water soluble salts of the metal components. One especially useful method of preparation of the catalysts of the present invention comprises forming an aqueous solution of $V_2O_5$ and adding a mixed suspension consisting of the calcined pre-formed iron-antimony composition, described hereinabove, bismuth compound and any optional metal compounds and optionally a catalyst support material, evaporating this to a thick paste, drying and calcining at an appropriate temperature and time period. Although the calcining temperature depends upon the starting materials, generally the calcining temperature may typically range between about 400° C. and 700° C. and preferably about 450° C. and 550° C.

Suitable catalyst support materials are known in the art and include silica, titania, alumnia, zirconia, silicon carbide, boron, phosphates and mixtures thereof. The now preferred support material is $TiO_2$.

The conversion of m-xylene to isophthalonitrile may be carried out in the same solid bed reactors in which phthalic acid or maleic acid anhydride are customarily produced. Further, the reactors may be fixed-bed, fluid bed or a transfer reactor using atmospheric, superatmospheric or subatmospheric pressure. Preferably the pressure used is near atmospheric pressure.

The reaction temperatures may range between about 250° C. and 500° C. and preferably between about 380° C. and 410° C., the exact value depending upon the precise composition of the catalyst.

The mole ratio of the reactants used in carrying out the ammoxidation reation can vary widely. For example, the mole ratio of molecular oxygen to the xylene such as m-xylene may typically range from about 2 to about 30 and the mole ratio of ammonia to the xylene may typically range from about 1 to about 10. A large excess of oxygen, as may be used in accordance with the invention, is not disadvantageous for the reaction and does not result in uncontrollable total combustion of ammonia and reaction products, when specific reaction conditions are maintained. The oxygen is preferably introduced in the form of air and since, in general, an inert atmosphere is not necessary. Alternatively, oxygen mixed with nitrogen and/or steam may be employed in place of air as the source of gaseous oxygen. The contact time typically ranges from about 0.1 to about 20 seconds or more and usually ranges from about 0.5 to about 15 seconds. The reaction products are condensed by cooling of the reaction gases, whereby there is obtained a solid product containing a small amount of moisture.

The invention will be further described in the following illustrative examples wherein all parts are by weight unless otherwise expressed.

EXAMPLES

All reactions were conducted in a 20 cc downward flow, fixed bed reactor. Off-gas rate was measured with a soap-film meter and the off-gas composition was determined with the aid of a Hewlett Packard gas chromatograph. After a short stabilization period, samples were collected over 7 minutes at periodic intervals. For the analysis of isophthalonitrile and m-xylene, the solvent in the collector vessel was acetone. Each sample was diluted with acetone to about 100 g. A weighted amount of tetralin was used as an internal standard in an approximate 5 g aliquot of the diluted solution. A 0.2 microliter sample was analyzed in a Varian model 3700 gas chromatograph fitted with a flame ionization detector and a SE-30 fused silica capillary column. The percentage of m-xylene conversion was determined by taking the ratio of moles of m-xylene reacted to the moles of m-xylene in the feed. The isophthalonitrile selectivity was determined by taking the ratio of moles of isophthalonitrile produced to the moles of m-xylene reacted. The Per Pass Conversion ("PPC") was calculated by multiplying the percentage of m-xylene converted by the isophthalonitrile selectivity.

The $TiO_2$ catalyst support material (duPont R) was calcined at 800° C. for 2 hours. This catalyst support material was used to prepare all of the catalysts used in the Examples.

The feed stocks were introduced into the reactor on a volume basis with the following ratios: m-xylene 1.0: air 65.2: $NH_3$ 6.8: $N_2$ 8.0.

EXAMPLE I

In this example of the present invention the antimony and iron were introduced into the catalyst as the pre-formed iron-antimony composition $Sb_{4.2}Fe_{2.1}O_x$. This pre-formed iron-antimony compound was prepared by refluxing a suspension of $Sb_2O_3$ (3.25 g) and $Fe(NO_3)_3.9H_2O$ (4.5 g) in 100 cc water and 30 cc of $HNO_3$, for 4 hours. The resulting mixture was evaporated to dryness and the obtained product was calcined at 750° C. for 2 hours.

The $V_2O_5$ (0.66 g) was dissolved in 20 cc of water which contained 10 g of oxalic acid by heating. A blue solution was obtained.

A mixed suspension consisting of the obtained $Sb_{4.2}Fe_{2.1}O_x$, $Bi(NO_3)_3.5H_2O$ (3.54 g) in 5 cc of $HNO_3$ and 30 cc of water was added to the above solution of $V_2O_5$ in which 30 g of the $TiO_2$ were added. The resulting mixture was then evaporated to a thick paste and dried in any oven at 110° C. The obtained catalyst was calcined at 500° C. for 4 hours. This catalyst had a formula of $V_1Sb_3Bi_{1.0}Fe_{1.5}O_x$ and was composed of 18% active catalyst and 82% $TiO_2$. The catalyst was mixed in a 50:50 ratio with quartz and the ammoxidation of m-xylene was carried out.

The results of using this catalyst of the present invention showing superior per pass conversion and isophthalonitrile selectivity are reported in TABLE I below.

EXAMPLE II (comparative example)

This example illustrates that the pre-forming of the iron-antimony composition produces unexpectedly superior results over the same catalyst made without pre-forming the iron and antimony.

The catalyst of Example II has the same overall chemical composition as the catalyst of Example I. It was prepared, however, without pre-forming any components thereof, as follows:

The catalyst was prepared by dissolving $V_2O_5$ (0.68 g) in 25 cc of water which contained 8 g of oxalic acid, by heating. A blue solution was obtained. The $SbCl_3$ (5.12 g) was hydrolyzed with 800 cc of water and the mixture was left standing. The resulting supernatant liquid was decanted and filtration was carried out, followed by washing with approximately 800 cc of water. The resulting white crystals were $Sb(OH)_3$.

A mixed suspension consisting of the above obtained $Sb(OH)_3$, $Bi(NO_3)_3.5H_2O$ (3.63 g) in 6 cc of $HNO_e$ and 18 cc of water and $Fe(NO_3)_3.9H_2O$ (4.53 g) in 20 cc $H_2O$ was added to the above solution of $V_2O_5$ in which 60 g of the $TiO_2$ were added. The mixture was then evaporated to a thick paste and dried in an oven at 110° C. The resulting dried catalyst was calcined at 500° C. for 4 hours. This catalyst had a formula of $V_{1.0}Sb_3Bi_{1.0}O_x$ and was composed of 18% active catalyst and 82% $TiO_2$. The catalyst was mixed in a 50:50 ratio with quartz and ammoxidation of m-xylene was carried out.

The results of using this catalyst for the production of isophthalonitrile is reported in TABLE I below.

The results in TABLE I below, show the much poorer per pass conversion and isophthalonitrile selectivity of this catalyst compared to the catalyst following the teachings of the present invention.

compounds to produce a catalyst containing the elements and proportions represented by the general formula:

$$V_1Bi_aSb_bFe_cX_dY_eZ_fO_g$$

wherein,
X=Mo, Cu, W, Nb, Te, P, Sn, Ge, As
Y=Co, Ni, Ce, La, Mn, Cr
Z=Alkali, alkaline earth, B, Tl and,
a=0.1–10, b=0.01–20, c=0.01–5, d=0–5, e=0–3, f=0–1, and g is determined by the valance requirements of the elements present.

2. The method of claim 1 wherein said catalyst includes a support.

3. The method of claim 2 wherein said catalyst support is selected from the group consisting of silica, titania, alumina, zirconia, silicon carbide, boron phosphate and mixtures thereof.

4. The method of claim 2 wherein said catalyst support is titania.

5. An ammoxidation catalyst composition having the general formula:

$$V_1Bi_aSb_bFe_cX_dY_eZ_fO_g$$

wherein,
X=Mo, Cu, W, Nb, Te, P, Sn, Ge, As
Y=Co, Ni, Ce, La, Mn, Cr
Z=Alkali, alkaline earth, B, Tl and,
a=0.1–10, b=0.01–20, c=0.01–5, d=0–5, e=0–3, f=0–1, and g is determined by the valance requirements of the elements present, said catalyst being further characterized in that said catalyst is prepared by pre-forming an iron-antimony oxide composition including calcining before admixture with the other catalyst components.

6. The catalyst composition of claim 5 wherein said

TABLE I

| EXPERIMENT No. | Catalyst Composition | Temperature (°C.) | Isophthalonitrile (ppc) (%) | Selectivity to isophthalonitrile (%) |
|---|---|---|---|---|
| I | 18% $V_1Sb_3Bi_1Fe_{1.5}O_x$ | 380 | 80.9 | 80.9 |
|   | 82% $TiO_2$ | 360 | 81.1 | 81.1 |
| II | 18% $V_1Sb_3Bi_1Fe_{1.5}O_x$ | 380 | 56.2 | 60.2 |
|   | 82% $TiO_2$ | 390 | 57.6 | 59.6 |
|   |   | 400 | 51.8 | 51.8 |

It will be appreciated that the instant specification and examples are set forth by way of illustration and not limitation and that various modifications and changes may be made without departing from the spirit and scope of the present invention.

What is claimed is:

1. A method for producing a catalyst suitable for ammoxidation comprising the steps of:
   a) forming an iron-antimony oxide composition including calcining and
   b) combining said composition with vanadium and bismuth compounds and optionally other metal catalyst composition further comprises a catalyst support.

7. The catalyst composition of claim 6 wherein said catalyst support is selected form the group consisting of silica, titania, alumina, zirconia, silicon carbide, boron phosphate and mixtures thereof.

8. The catalyst composition of claim 6 wherein said catalyst support is titania.

9. The catalyst composition of claim 5 wherein said catalyst has the formula $V_1Sb_3Bi_{1.0}Fe_{1.5}O_g$.

* * * * *